(12) United States Patent  
Schmitt et al.

(10) Patent No.: US 7,848,791 B2  
(45) Date of Patent: Dec. 7, 2010

(54) OPTICAL COHERENCE TOMOGRAPHY APPARATUS AND METHODS

(75) Inventors: Joseph M. Schmitt, Andover, MA (US); Amanda Koski, Westford, MA (US); Michael Atlas, Arlington, MA (US); Christopher Petersen, Carlisle, MA (US)

(73) Assignee: LightLab Imaging, Inc., Westford, MA (US)

( * ) Notice: Subject to any disclaimer, the term of this patent is extended or adjusted under 35 U.S.C. 154(b) by 834 days.

(21) Appl. No.: 11/351,896

(22) Filed: Feb. 10, 2006

(65) Prior Publication Data

US 2006/0241503 A1 Oct. 26, 2006

Related U.S. Application Data

(60) Provisional application No. 60/651,831, filed on Feb. 10, 2005.

(51) Int. Cl.
*A61B 6/00* (2006.01)

(52) U.S. Cl. .............. 600/476; 600/478; 600/473; 356/357; 356/358; 356/345; 356/497

(58) Field of Classification Search .......... 600/473, 600/476, 478; 182/2; 356/357, 358, 345, 356/497
See application file for complete search history.

(56) References Cited

U.S. PATENT DOCUMENTS

| | | | |
|---|---|---|---|
| 4,375,818 A * | 3/1983 | Suwaki et al. | 600/463 |
| 4,445,892 A | 5/1984 | Hussein et al. | |
| 4,569,335 A | 2/1986 | Tsuno | |
| 4,754,752 A | 7/1988 | Ginsburg et al. | |

(Continued)

FOREIGN PATENT DOCUMENTS

JP 2002-214127 7/2002

OTHER PUBLICATIONS

International Preliminary Report on Patentability and Written Opinion of the International Searching Authority, International Application No. PCT/US2006/004863, mailed Aug. 23, 2007.

(Continued)

*Primary Examiner*—Long V Le  
*Assistant Examiner*—Joel F Brutus  
(74) *Attorney, Agent, or Firm*—K & L Gates LLP

(57) ABSTRACT

In one aspect, the invention relates to an imaging probe. The imaging probe includes an elongate body having a proximal end and distal end, the elongate body adapted to enclose a portion of a slidable optical fiber, the optical fiber having a longitudinal axis; and a first optical assembly attached to a distal end of the fiber. The first optical assembly includes a beam director adapted to direct light emitted from the fiber to a plane at a predetermined angle to the longitudinal axis, a linear actuator disposed at the proximal portion of the elongated body, the actuator adapted to affect relative linear motion between the elongate body and the optical fiber; and a second optical assembly located at the distal portion of the elongate body and attached thereto, the second optical assembly comprising a reflector in optical communication with the first optical assembly, the reflector adapted to direct the light to a position distal to the elongate body.

17 Claims, 11 Drawing Sheets

U.S. PATENT DOCUMENTS

| | | | |
|---|---|---|---|
| 4,762,129 | A | 8/1988 | Bonzel |
| 4,878,893 | A | 11/1989 | Chin |
| 5,116,317 | A | 5/1992 | Carson, Jr. et al. |
| 5,321,501 | A | 6/1994 | Swanson et al. |
| 5,459,570 | A | 10/1995 | Swanson et al. |
| 5,465,147 | A | 11/1995 | Swanson |
| 5,526,822 | A * | 6/1996 | Burbank et al. ............ 600/567 |
| 5,748,598 | A | 5/1998 | Swanson |
| 5,757,763 | A | 5/1998 | Green, Jr. et al. |
| 5,784,352 | A | 7/1998 | Swanson et al. |
| 5,854,710 | A | 12/1998 | Rao et al. |
| 5,956,355 | A | 9/1999 | Swanson et al. |
| 6,075,601 | A * | 6/2000 | Marcus et al. ............ 356/497 |
| 6,111,645 | A | 8/2000 | Tearney et al. |
| 6,134,003 | A | 10/2000 | Tearney et al. |
| 6,160,826 | A | 12/2000 | Swanson et al. |
| 6,191,862 | B1 | 2/2001 | Swanson et al. |
| 6,282,011 | B1 | 8/2001 | Tearney et al. |
| 6,421,164 | B2 | 7/2002 | Tearney et al. |
| 6,445,939 | B1 | 9/2002 | Swanson et al. |
| 6,450,964 | B1 * | 9/2002 | Webler ............ 600/467 |
| 6,468,243 | B1 | 10/2002 | Miyagawa et al. |
| 6,485,413 | B1 * | 11/2002 | Boppart et al. ............ 600/160 |
| 6,501,551 | B1 | 12/2002 | Tearney et al. |
| 6,552,796 | B2 | 4/2003 | Magnin et al. |
| 6,564,087 | B1 * | 5/2003 | Pitris et al. ............ 600/478 |
| 6,570,659 | B2 | 5/2003 | Schmitt |
| 6,608,684 | B1 | 8/2003 | Gelikonov |
| 6,814,727 | B2 | 11/2004 | Mansouri-Ruiz |
| 6,879,851 | B2 | 4/2005 | McNamara et al. |
| 6,891,984 | B2 | 5/2005 | Petersen et al. |
| 2001/0019762 | A1 | 9/2001 | Nazarova et al. |
| 2002/0077564 | A1 | 6/2002 | Campbell et al. |
| 2003/0069549 | A1 | 4/2003 | MacMahon et al. |
| 2003/0077043 | A1 * | 4/2003 | Hamm et al. ............ 385/72 |
| 2004/0092830 | A1 | 5/2004 | Scott et al. |

OTHER PUBLICATIONS

B. Bouma, et al., "High Resolutin Imaging of the Human Esophagus and Stomach Using Optical Coherence Tomography," Gastrointest Endosc. 2000; 51:467-474.

International Search Report, International Application No. PCT/US2006/004863, Mailed Jun. 29, 2006, 7 pgs.

International Search Report, International Application No. PCT/US2006/004863, mailed Aug. 30, 2006, 15 pgs.

* cited by examiner

OPTICAL COHERENCE TOMOGRAPHY APPARATUS AND METHODS

RELATED APPLICATIONS

This application claims priority to U.S. Provisional Patent Application 60/651,831 filed on Feb. 10, 2005, the disclosure of which is herein incorporated by reference in its entirety.

FIELD OF THE INVENTION

This invention relates to the field of optical imaging and more specifically to the design of fiber-optic probes for optical coherence tomography (OCT) and other optical imaging technologies.

BACKGROUND OF THE INVENTION

As the demand for less invasive medical diagnosis and treatment grows, techniques for examining living tissue on a microscopic scale have become increasingly important. Conventional medical endoscopes, with diameters that range from about 1 mm to over 1 cm, provide physicians with a view of the surface of the walls of lumens in the gastrointestinal, pulmonary, and reproductive tracts. However, seeing below the surface of the tissue is essential to detect and characterize lesions associated with cancer and other pathological conditions. Optical Coherence Tomography (OCT), an interferometric imaging technology, is ideally suited to subsurface visualization of biological tissue via small-diameter probes and catheters.

Existing OCT scanning methods have primarily relied on galvanometers to scan the probe beam linearly across the target material. Alternatively, existing systems use a rotary motor to scan the probe beam circumferentially inside a lumen with a circular cross section. Neither method satisfies the need to view targets in front of the probe through a narrow orifice. As a result, a specific need exists for a probe that can visualize blocked coronary arteries, with the goal of characterizing the composition of the plaque and guiding atherectomy devices designed to dissect or remove the blockage. A need also exists for an OCT probe for insertion in a needle that would allow an operator to view tissue structures as the needle advances. A further need exists for probes that can be inserted through working channels of endoscopes designed for forward-directed imaging.

To the extent that forward-directed optical scanning is possible, such implementations are impractical for many applications. This follows because they generate non-linear scan patterns that are difficult to interpret, require complex and expensive mechanisms, or require probes with excessively large diameters. Furthermore, systems that depict actuators and movable mechanisms positioned at or near the distal end of the fiber endoscope conflict with the need to make the distal end as small as possible. What is needed, therefore, is a catheter design that enables forward-directed scanning at a distal location such that the distal portion of the probe can be significantly miniaturized and simplified compared to the known art.

SUMMARY OF THE INVENTION

The invention relates to methods and apparatus for imaging biological tissues and other materials using small-diameter, forward-looking probes. The disclosed methods are based on a push-pull actuation scheme that advantageously overcomes many of the limitations of previous approaches. In particular, the probe designs and associated actuation methods disclosed herein enable forward-directed imaging through catheters with diameters small enough to be placed in coronary arteries, small-gauge needles, and/or working channels of miniature endoscopes.

In one aspect, the invention relates to an imaging probe that includes a single-mode optical fiber with an integrated microlens and beam deflector that moves longitudinally back and forth inside a flexible transparent tube. The side-scanning beam is re-directed by a stationary prism or mirror to produce a cross-sectional OCT scan of objects in front of the tip of the catheter.

In another aspect of the invention relates to a probe that includes an angle-polished, single-mode optical fiber that moves longitudinally back and forth inside a flexible transparent tube to which a mirror and a stationary lens assembly are attached. Located at the tip of the tube, the lens assembly focuses the beam onto a target in front of the tube to produce a cross-sectional OCT scan.

In one aspect, the invention relates to an imaging probe. The imaging probe includes an elongate body having a proximal end and distal end, the elongate body adapted to enclose a portion of a slidable optical fiber, the optical fiber having a longitudinal axis, and a first optical assembly attached to a distal end of the fiber. The first optical assembly includes a beam director adapted to direct light emitted from the fiber to a plane at a predetermined angle to the longitudinal axis, a linear actuator disposed at the proximal portion of the elongated body, the actuator adapted to affect relative linear motion between the elongate body and the optical fiber, and a second optical assembly located at the distal portion of the elongate body and attached thereto, the second optical assembly comprising a reflector in optical communication with the first optical assembly, the reflector adapted to direct the light to a position distal to the elongate body.

There are various embodiments and implementations of this aspect of the invention For example, the position of the reflector can be adapted to cause the light to scan in a forward-viewing direction in response to the relative linear motion. The probe further can further include a stationary core that substantially encircles the elongate body, the stationary core adapted to change an imaging position at a catheter tip in response to rotation of the stationary core. The first optical assembly can further include a focusing micro-lens disposed at a tip of the optical fiber and a single reflector disposed within the elongate body such that the reflector is inclined at an angle that substantially improves the forward viewing angle and length of the scanning beam, wherein the lens and reflector form an imaging plane located distal to the distal end of the elongate body and oriented substantially orthogonal to the longitudinal axis of the fiber. The reflector and an optical window can be constructed from a block of optical transparent material that attaches to the elongate body.

Additionally, the first optical assembly can include an optical fiber with an angle-polished tip and the second optical assembly can include the reflector with a pair of micro-lenses in a housing that attaches to the outside of the elongate body. The focal lengths and the positions of the lenses can be chosen to achieve a desired focal spot size and working distance. The optical assembly can include an optical fiber with an angle-polished tip and a reflector with a single gradient-index lens in a housing that attaches to the outside of the elongate body, the index profile and position of the gradient-index lens selected to achieve a desired focal spot size and working distance. The linear actuator can include a voice coil.

Furthermore, in one embodiment, the linear actuator is adapted to cause the sheath to move while the fiber remains stationary with respect to the actuator. The elongate body can be fluid-filled and adapted to move back and forth around the optical fiber. The probe can further include a metal tube that substantially ensheaths the optical fiber, except at its tip where light emerges, and an outer fluid-filled sheath that is adapted to moves relative to the metal tube and optical fiber. In one embodiment, the probe is configured for use in a sample arm of an optical coherence tomography system for applications related to scanning biological tissue.

The reference or the sample arm of an optical coherence tomography system can include path length adjustment means, wherein such means automatically compensate optical path length changes induced by actuator scanning. The beam can scan along a line in synchrony with the linear motion of the actuator. The elongate body can further include a curved tip, at least a portion of the tip adapted to emit light in response to the linear motion.

In another aspect, the invention relates to an optical coherence tomography forward scanning system. The system includes a linear actuator, a single mode optical fiber having an angled endface, the fiber mechanically coupled to the linear actuator, and a sheath having a reflector disposed at an angle such that motion of the optical fiber endface relative to the reflector directs light from the endface to a plane substantially parallel to a circular cross-section of the fiber. The system, can further include an optical fiber rotational strain relief apparatus, the apparatus in mechanical communication with the fiber.

In another aspect, the invention relates to optical fiber rotational strain relief apparatus. The apparatus includes a tube having a first port and a second port, the tube arranged to form at least one loop portion, wherein the first port is adapted for coupling to an optical coherence tomography imaging probe, the interior of the tube adapted to facilitate sliding of an optical fiber. The second port can be adapted for coupling to a sample arm of an interferometer. The loop portion can be substantially circular.

An important feature of the some embodiments of the aforementioned aspects is their compatibility with therapeutic devices designed for atherectomy, prostectomy and other clinical procedures that would benefit from image guidance inside blood vessels and small body cavities.

In yet another aspect of the invention, suitable for imaging surfaces of exposed tissues, includes a single-mode optical fiber with an integrated micro-lens and beam deflector that translate longitudinally back and forth inside a transparent plastic tube. The tip of the tube is formed into the shape of a U, with the beam directed downward at the base of the tip. Longitudinal movement of the optical fiber generates a forward-directed linear scan.

Additional aspects of the invention includes of methods of fabricating the probes and the actuation mechanisms that enable control of the orientation, amplitude, and repetition rate of the scanning beam.

It should be understood that the terms "a," "an," and "the" mean "one or more," unless expressly specified otherwise.

The foregoing, and other features and advantages of the invention, as well as the invention itself, will be more fully understood from the description, drawings, and claims which follow.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. The drawings associated with the disclosure are addressed on an individual basis within the disclosure as they are introduced.

The claimed invention will be more completely understood through the following detailed description, which should be read in conjunction with the attached drawings. In this description, like numbers refer to similar elements within various embodiments of the present invention.

DETAILED DESCRIPTION

The following description refers to the accompanying drawings that illustrate certain embodiments of the present invention. Other embodiments are possible and modifications may be made to the embodiments without departing from the spirit and scope of the invention. Therefore, the following detailed description is not meant to limit the present invention. Rather, the scope of the present invention is defined by the appended claims.

It should be understood that the order of the steps of the methods of the invention is immaterial so long as the invention remains operable. Moreover, two or more steps may be conducted simultaneously or in a different order than recited herein unless otherwise specified.

In general, the aspects and embodiments of the invention disclosed herein relate to imaging system components. Specifically, the aspect of the invention include components, such as probes, push-pull devices, actuators, coils, mechanical linkages and other components suitable for use in imaging systems based on optical coherence tomography (OCT), fluorescence, Raman spectroscopy, or other types of optical detection methods. As an example, FIG. 1 shows an OCT system 10 designed to accommodate forward-scanning fiber-optic probes actuated by a push-pull mechanism and other appropriate components as desirable.

Figure 1:
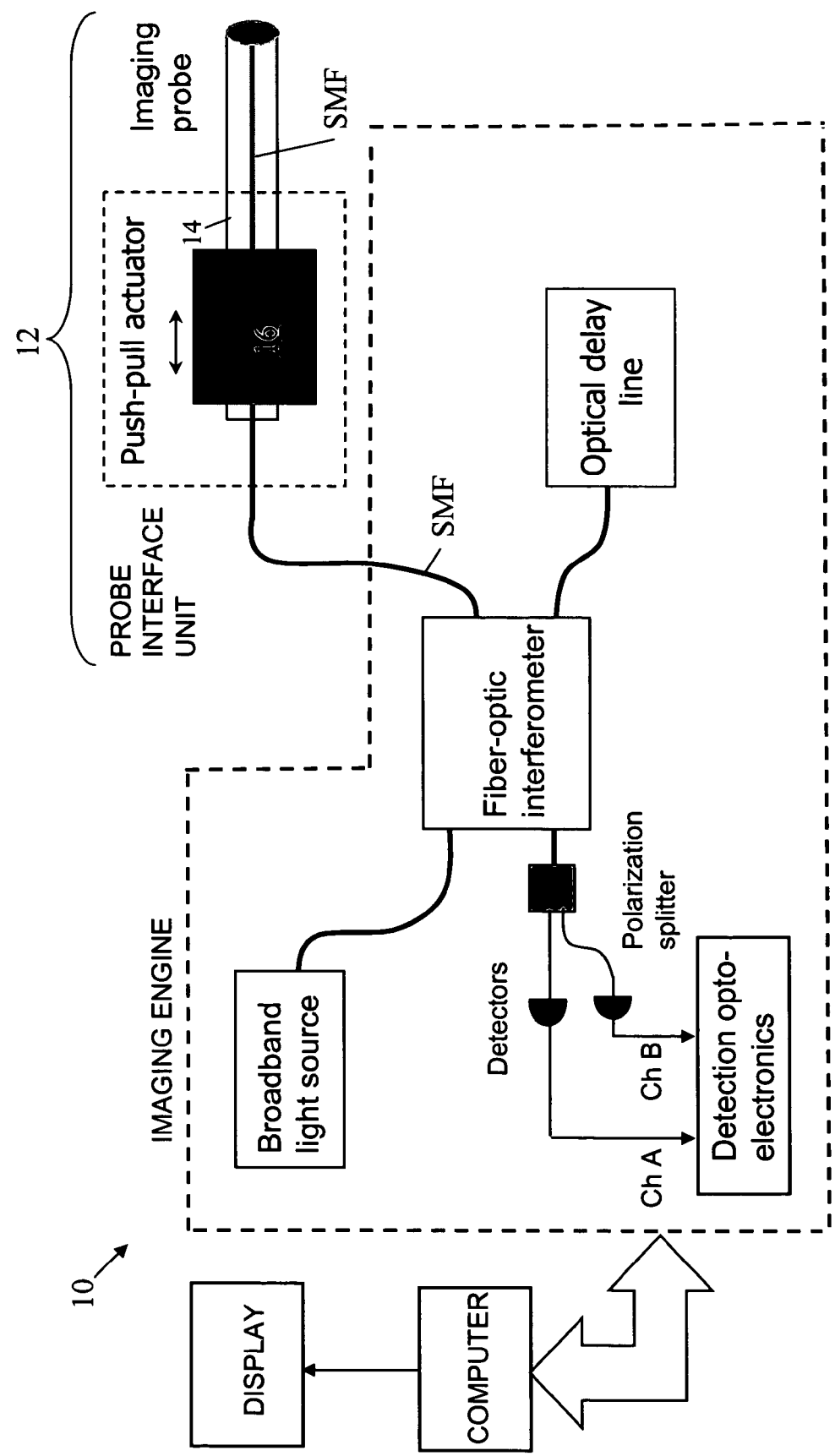
FIG. 1 is a schematic diagram of an optical coherence tomography (OCT) system coupled with a push-pull actuator and probe according to an illustrative embodiment of the invention.

As shown in FIG. 1, light from a broadband source is split by a fiber-optic interferometer into reference and sample beams. To provide the axial component of the scan, an optical delay line varies the length of the optical path in the reference arm. Interference of the reference and sample beams is detected via two orthogonal polarization channels. The interference signals generated in each channel can be combined to ensure insensitivity to polarization changes in the sample arm. Alternatively, the signals can be processed separately to extract information about the polarization properties of the sample.

In one aspect, the invention relates to the subsystem 12 and portions thereof that includes a push-pull actuator and imaging probe suitable for coupling to the sample arm, which together provide the transverse component of the scan. As shown, the subsystem 12 receives a single mode fiber SMF from the interferometer which is slidably disposed in an elongate body 14 to form a portion of an imaging probe. In some embodiments, the single mode fiber SMF is surrounded by and/or adhered to a durable sleeve, such as a metal tube. In turn, a push-pull actuator 16 is present to affect the slidable motion of the single mode fiber relative to the elongate body. The subsystem allows for proximal mechanical actuation which in turn allows the size of the catheter tip to remain small. Typically, a beam director or other optical assembly is attached to the distal end of the single mode optical fiber. Additional details relating to the underlying concept of the push-pull forward scanning imaging probe are discussed with respect to FIG. 2.

Figure 2:
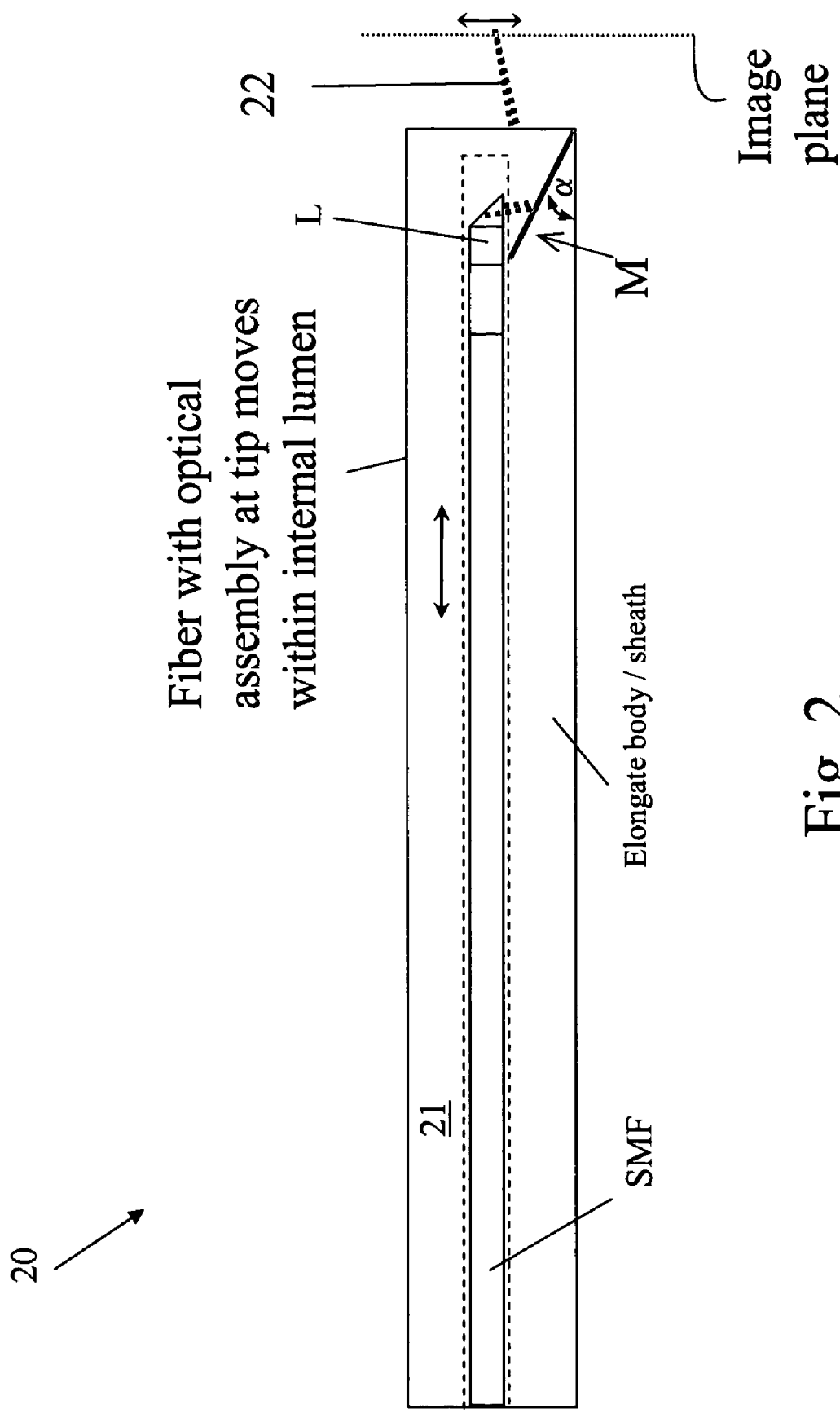
FIG. 2 is a schematic diagram that depicts a forward scanning imaging probe according to an illustrative embodiment of the invention.

As shown in FIG. 2, a probe portion 20 is illustrated that includes an elongate body 21, such as a lumen or tube that contains an optical fiber SMF suitable for transmitting light to and receiving light from a sample. The fiber is slidably disposed within the elongate body 21 as shown by the double headed arrow indicating slidable degrees of freedom relative to the elongate body. The tip of the fiber is polished at an angle (typically about 40 to about 45 degrees) to permit a focused beam 22 to exit from the side of the fiber. An optical fiber with integrated lens L and beam director, such as the polished fiber tip, is particularly well suited to this application. In one aspect, the present invention includes a single-mode optical fiber with an integrated micro-lens and beam deflector that moves longitudinally back and forth inside a flexible transparent tube. The side-scanning beam is re-directed by a stationary prism or mirror M to produce a cross-sectional OCT scan of objects in front of the tip of the catheter.

The beam 22 is redirected forward along the longitudinal axis of the fiber by a mirror, inclined at angle α (also, typically about 40 to about 45 degrees). Longitudinal movement of the sheath relative to the fiber at a constant speed causes the beam to scan a line uniformly in the forward image plane. Relative motion can be accomplished either by keeping the tube stationary as the optical fiber translates or by keeping the optical fiber stationary as the tube translates. The latter approach offers mechanical advantages which will be made clear in more detail below. Movement of the tube 21 relative to the sheath is preferred, because this configuration allows the operator to adjust the azimuthal plane of the scan by rotating the fiber from the proximal end, without interfering with the push-pull motion. For α=45°, the length of the path of the sample beam to the image plane is constant over the scan and the length of the scan in the image plane equals the linear distance at which the tube translates relative to the fiber.

In general, the image plane is positioned distal to the end of a catheter in order to facilitate substantially forward scanning. As an example, if an elongate body, such as a portion of a catheter or sheath, is disposed in artery having a blockage, once the elongate body reaches the artery, forward scanning of the blockage is possible. In such an example, some or all of the image plane can be disposed on the blockage.

One simple and inexpensive method of fabricating the side mirror M depicted in FIG. 2 is to mold a short length of optical fiber with an angle-polished and coated tip inside the tube that translates over the internal optical fiber SMF. For α=45°, the available scan length approximately equals the diameter of the fiber used to fabricate the side mirror. In one embodiment, the optical fiber used in the probe is both slidably and rotatably disposed inside the elongate body. Thus, in one aspect, the invention enables the conversion of a linear motion to forward optical scanning, with the associated control, vibration reduction, and reduced optical losses.

Figure 3:
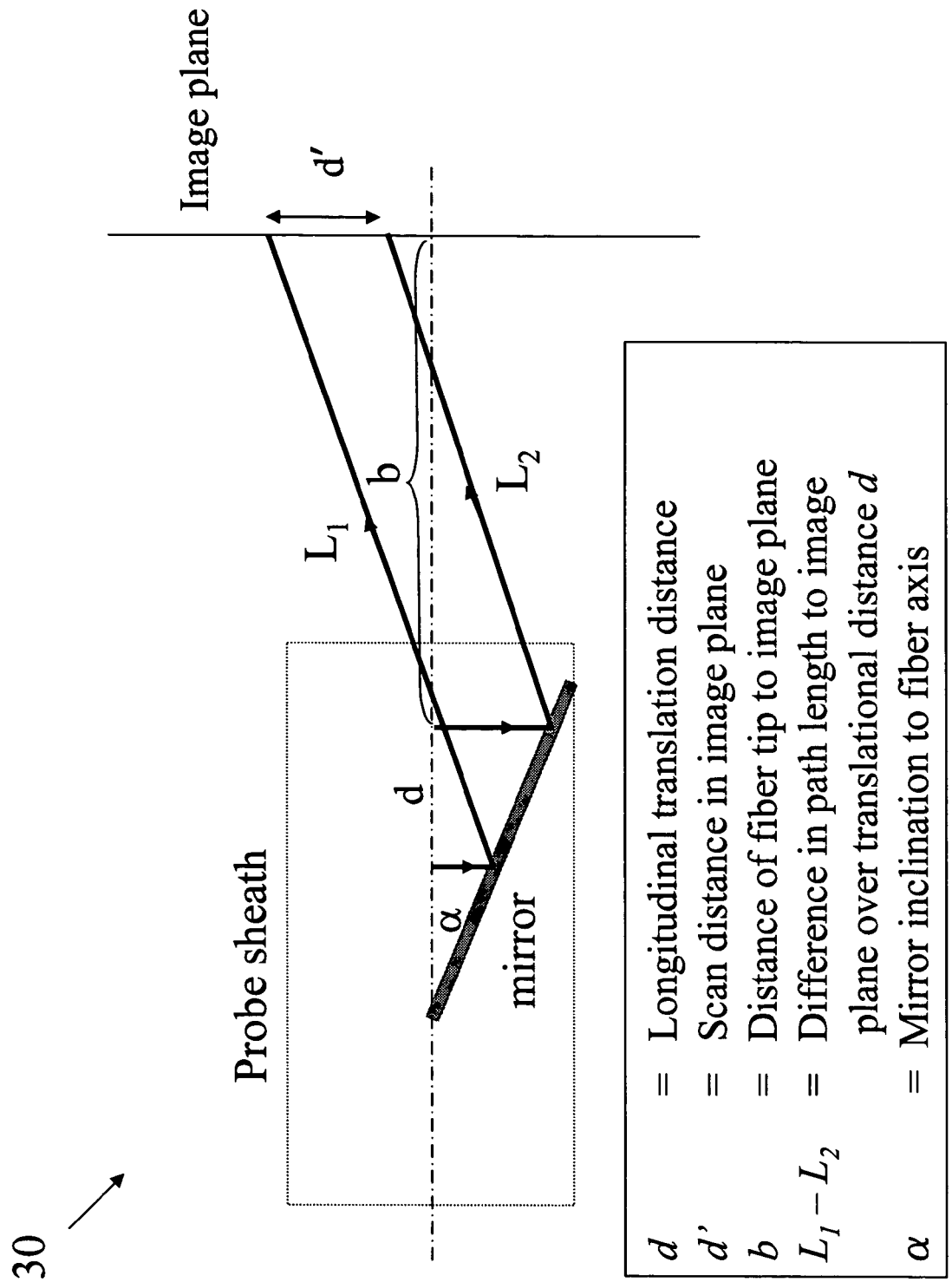
FIG. 3 is a schematic diagram that defines an optical component arrangement incorporated in an illustrative embodiment of the invention.

Various embodiments of the basic conceptual arrangement illustrated in the probe 20 of FIG. 2 are possible. As depicted in the probe portion 30 of FIG. 3, the angle of inclination α can be set at an angle less than 45° to utilize the cross-sectional area occupied by the probe more efficiently. As a decreases, the scan line in the image plane shifts closer to the longitudinal axis of the probe. According to the definitions in FIG. 3, the relationship between the scan distance in the image plane and the longitudinal translation distance is given by d'=d tan α. For α≠0°, the path length of the sample beam to the image plane varies linearly over the length of the scan, according to $$\Delta L = L_1 - L_2 = d\tan\alpha + \frac{b-d}{\cos(90° - 2\alpha)} \quad [\text{Eq. 1}]$$

where b is the distance from the fiber tip at its full extension to the image plane (FIG. 3). This linear variation can be compensated before display by the OCT scan conversion software. In addition, the reference arm can include automated translation to compensate for the change in path length.

Figure 4A:
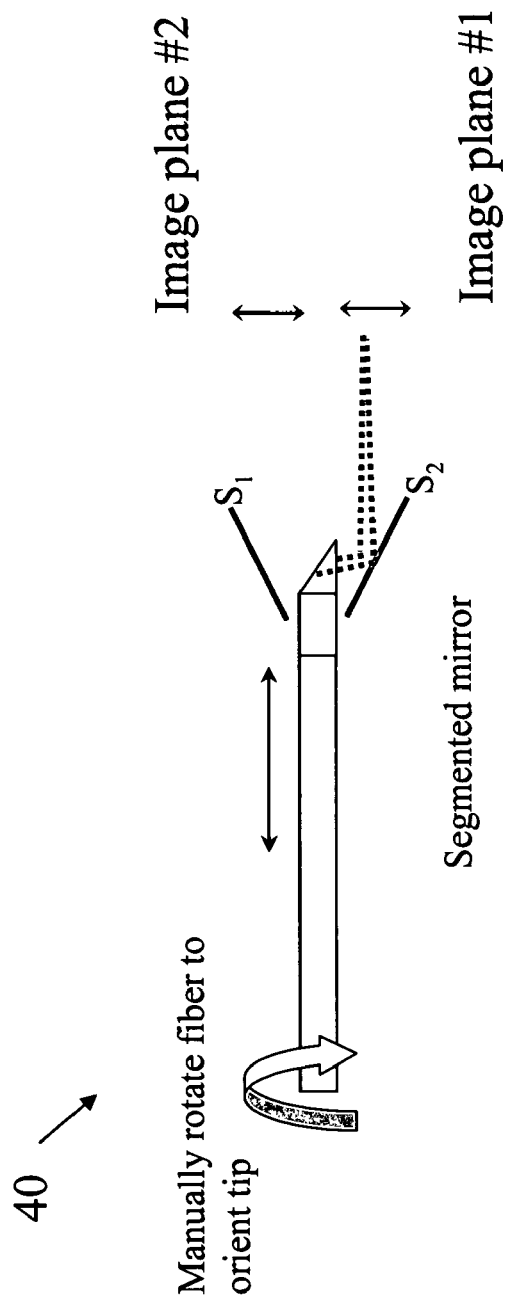
FIGS. 4A-4B are schematic diagrams that depict a version of the forward-scanning probe that allows angular rotation of the scanning plane according to an illustrative embodiment of the invention.
Figure 4B:
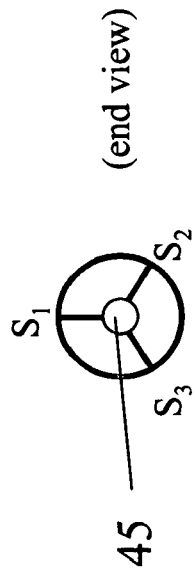

FIG. 4A shows a fiber portion 40 illustrating an extension of the concept depicted in FIG. 2. FIG. 4B shows an end view of a probe embodiment. In this system, three mirror segments $S_1$, $S_2$, and $S_3$ are arranged in a corner-cube apparatus configuration to permit the operator to select one of three different azimuthal planes in the image plane by rotating the fiber. The fiber passes through a hole 45 in the center of the mirror assembly. Depending on the requirements of specific applications, mirrors with a different number of segments can also be used. A variety of methods can be used to construct the segmented mirror. For example, a set of mirrors fabricated from short lengths of angle-polished and coated optical fibers can be inserted into the wall of tube that translates over the internal optical fiber. Alternatively, the facets of the mirror can be molded into a solid block of plastic or ceramic and coated with a metallic reflector. For ease of assembly, the tip of the push-pull probe can be manufactured as a unit separate from the mirror assembly. By translating the sheathed fiber to relative to the mirror, the scan length in the forward plane can be adjusted manually by the operator.

Figure 5A:
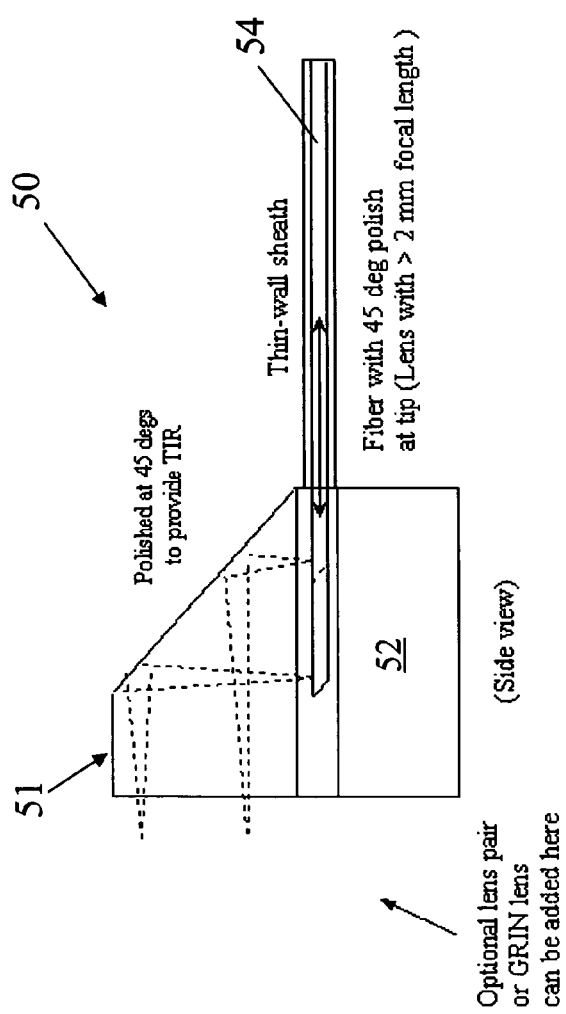
FIGS. 5A-5B are schematic diagrams that depict a forward-scanning probe according to an illustrative embodiment of the invention.
Figure 5B:
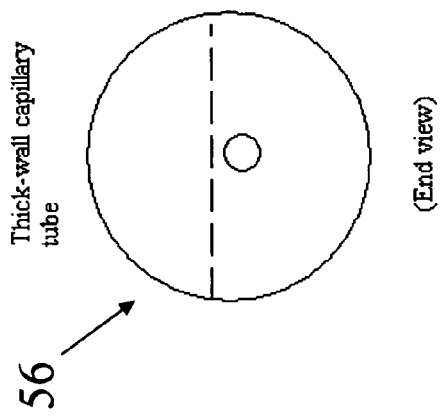

FIGS. 5A-7 depict additional embodiments of the forward scanning push-pull probe implementation discussed above. In FIGS. 5A-5B, in the probe embodiment 50, the angled mirror is formed by polishing a flat region 51 at the distal end of in a solid rod of glass or transparent plastic 52. The flat 51 can either be left uncoated, wherein the beam deflects by total internal reflection, or it can be coated with a dielectric or metallic film to reduce sensitivity to contamination of the surface. The tip of an optical fiber 54, which contains an integral lens and beam deflector, inserts into a hole drilled in the rod 52. To reduce the demands of machining on small dimensions, the entire assembly can be molded in glass or plastic. This latter method of fabrication lends itself to mass production of disposable probes.

Figure 6:
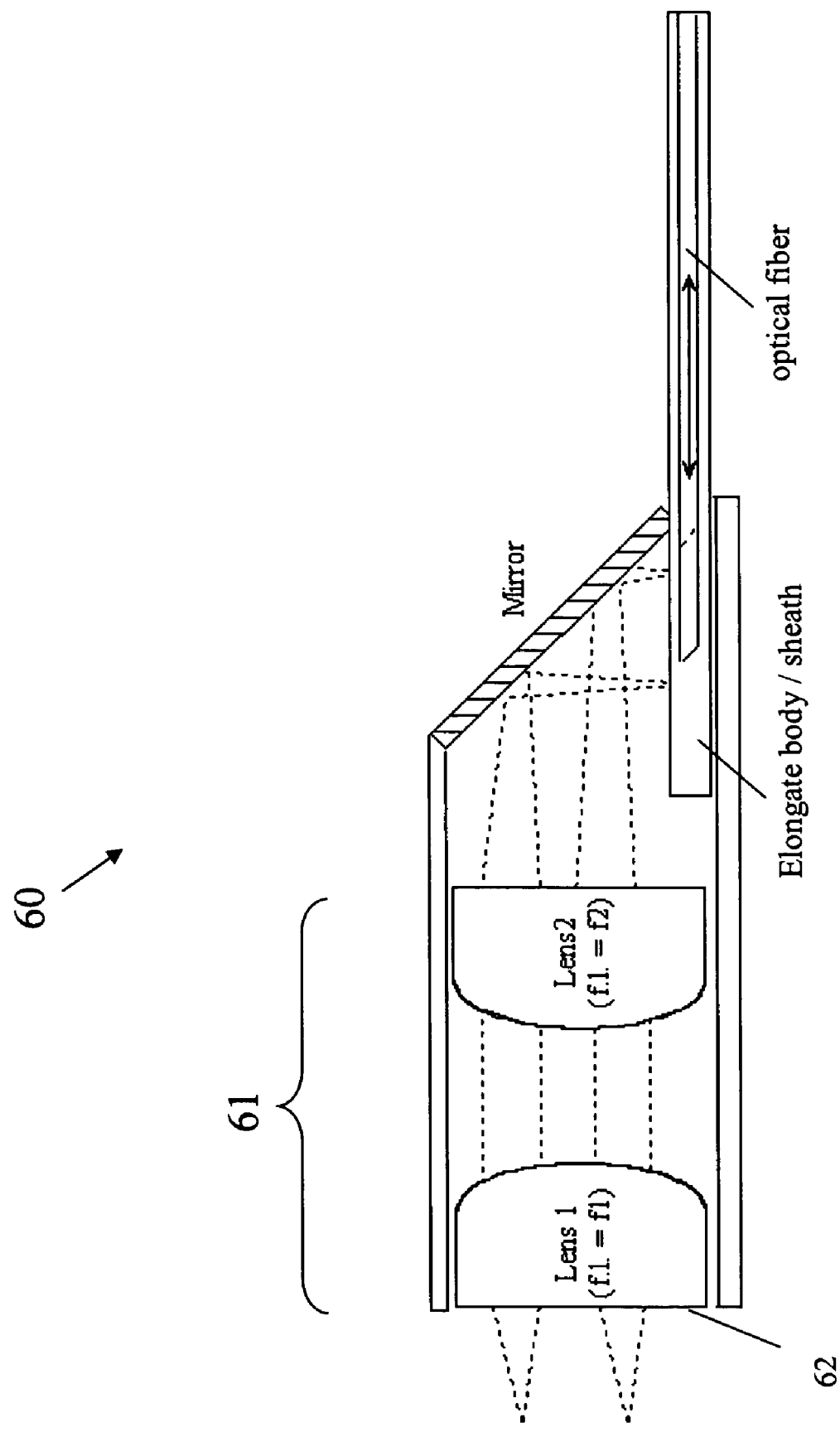
FIG. 6 is a schematic diagram that depicts a forward-scanning probe that employs a pair of lenses to adjust the focal distance and spot size of the scanning beam according to an illustrative embodiment of the invention.
Figure 7:
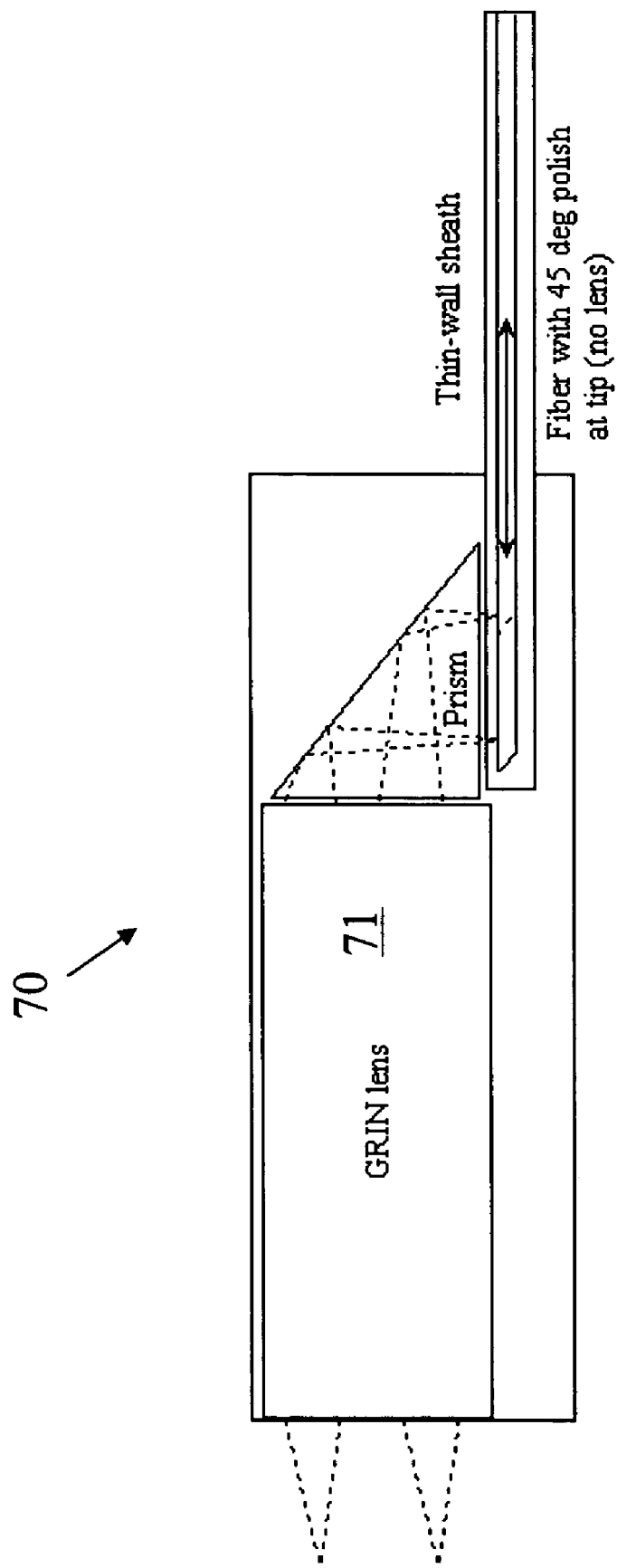
FIG. 7 is a schematic diagram that depicts a forward-scanning probe that employs a gradient-index lens to adjust the focal distance and spot size of the scanning beam according to an illustrative embodiment of the invention.

In certain applications, especially those requiring the probe beam to focus tightly at a long working distance, an external lens assembly can be used in place of the lens and beam deflector integrated into the tip of the optical fiber. FIG. 6 shows an example of a probe portion 60 with such a lens assembly 61 that includes an optical window 62. In this embodiment, diverging light exits the side of the angle-polished fiber, reflects from the external mirror, and passes through a pair of piano-convex or aspheric lenses that focus the beam at a specified distance in front of the probe. Since the pair of lenses images the core of the fiber onto the focal plane, the spot size is proportional to $d_0 f_1/f_2$, where $d_0$ is the diameter of the core of the fiber and $f_1/f_2$ is the ratio of the focal lengths of the lens. Therefore, the lateral resolution of the probe can be set by selecting a pair of lenses with the desired focal lengths. In one embodiment, the lenses are selected such that the focal spot size ranges from about 5 to about 40 μm and the working distance ranges from about 0.5 to about 5 cm. Alternatively, to simplify construction, in another probe embodiment 70 an imaging graded-index (GRIN) lens 71 with optical characteristics similar to a pair of plan-convex lenses can also be employed as shown in FIG. 7.

Figure 8A:
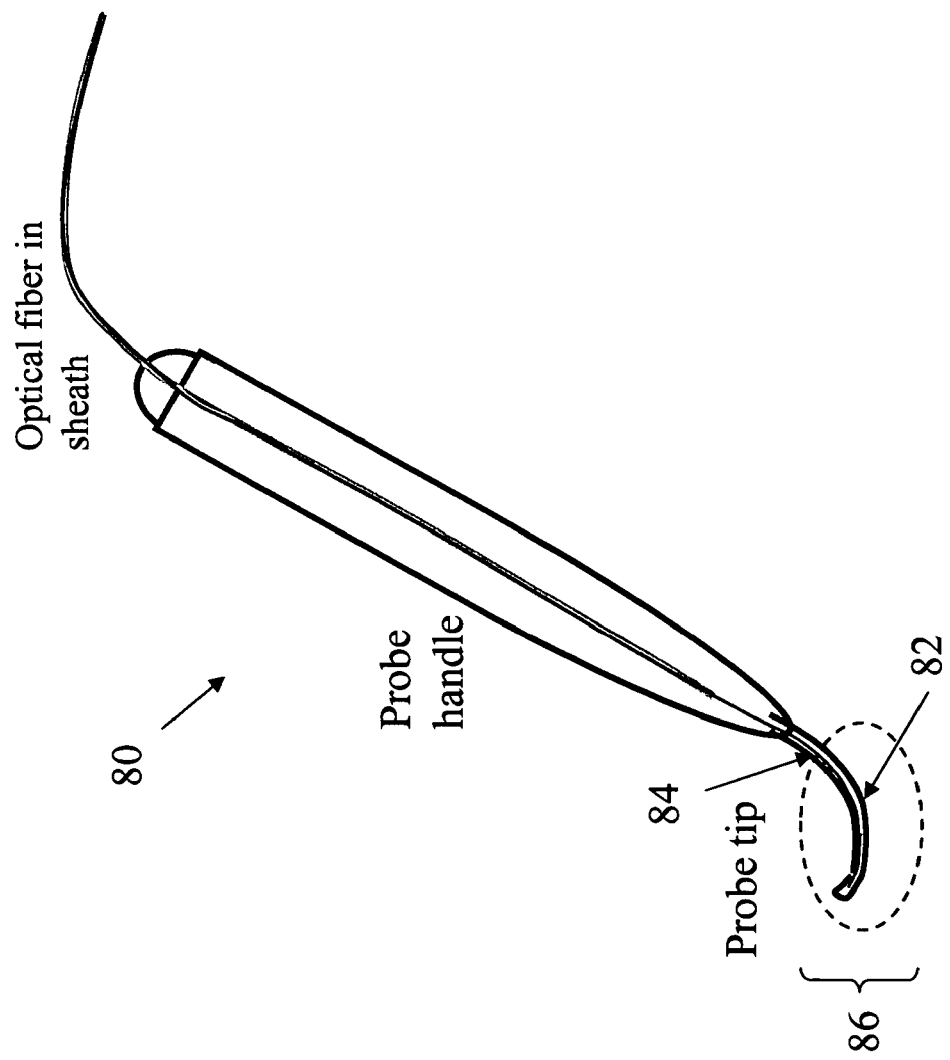
FIGS. 8A-8B are schematic diagrams that depict a forward-scanning probe designed for handheld operation according to an illustrative embodiment of the invention.
Figure 8B:
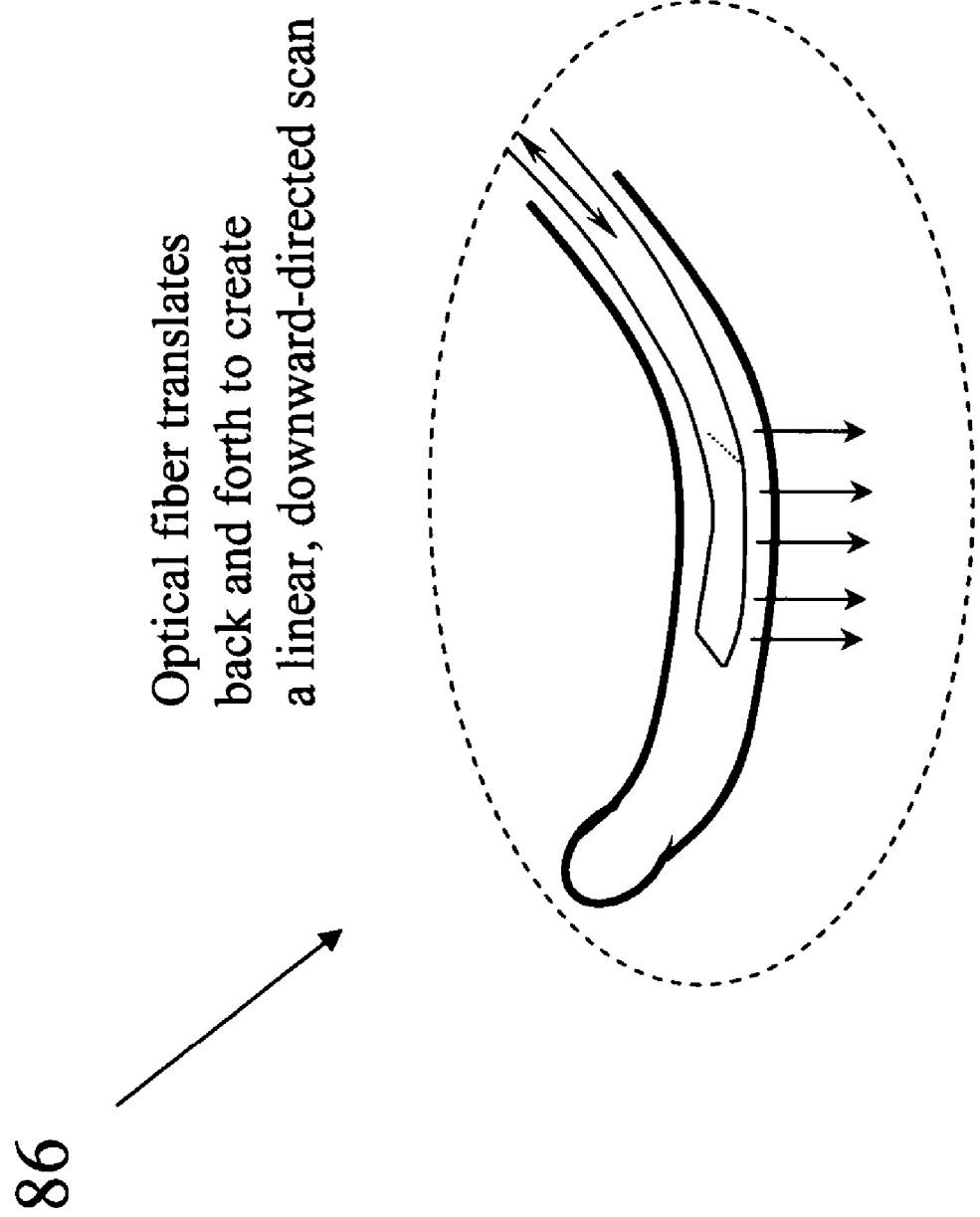

FIGS. 8A-8B depict another system 80 to generate a forward-scanning beam, which lends itself to application in a handheld probe. In this embodiment, a curve 82 is formed in the tube 84 containing the translating fiber core. The tube fits inside the tip of a probe 86, which has a slot at its base through which the beam exits. The probe is designed for imaging organs that are accessible from the surface of the body or through narrow incisions. During minimally invasive surgery, for example, the tip of the probe 86 can be positioned close to the area of interest without blocking the field of view of the surgeon. For endoscopic applications, the handle can be removed and a bend formed in the region of the tube through which the probe beam passes. These alterations allow the probe to be straightened for insertion through the working channel of an endoscope. Upon exit from the endoscope, the preformed tip enables the imaging probe to rest against the side of the tissue, without requiring flexion of the endoscope.

Figure 9:
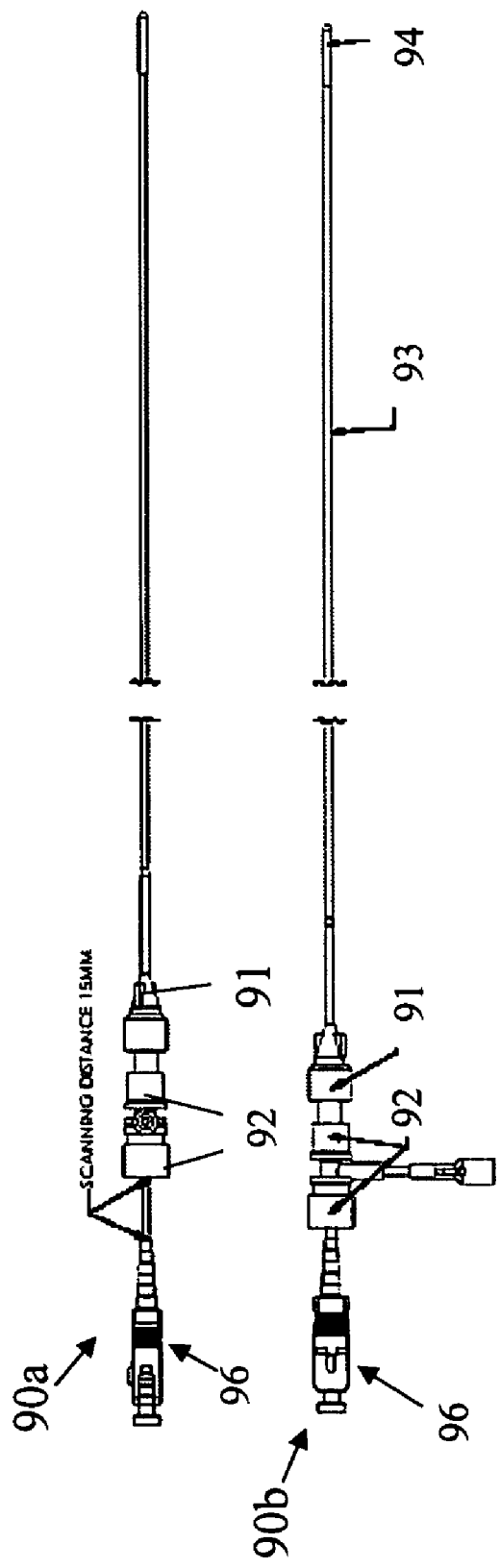
FIG. 9 is a schematic diagram that shows a group of embodiments of a push-pull mechanical linkage according to an illustrative embodiment of the invention.

FIG. 9 shows two systems 90a, and 90b using the push-pull mechanical linkage that can be implemented in various embodiments of the forward-scanning probe (FIGS. 5-8). The systems 90a and 90b have a common 'Luer' element 91. A T-fitting with an O-ring assembly 92 is also depicted. In system 90b, a heat bonded sheath assembly 93 that contains the optical fiber is shown in communication with a tubing portion 94.

Figure 10:
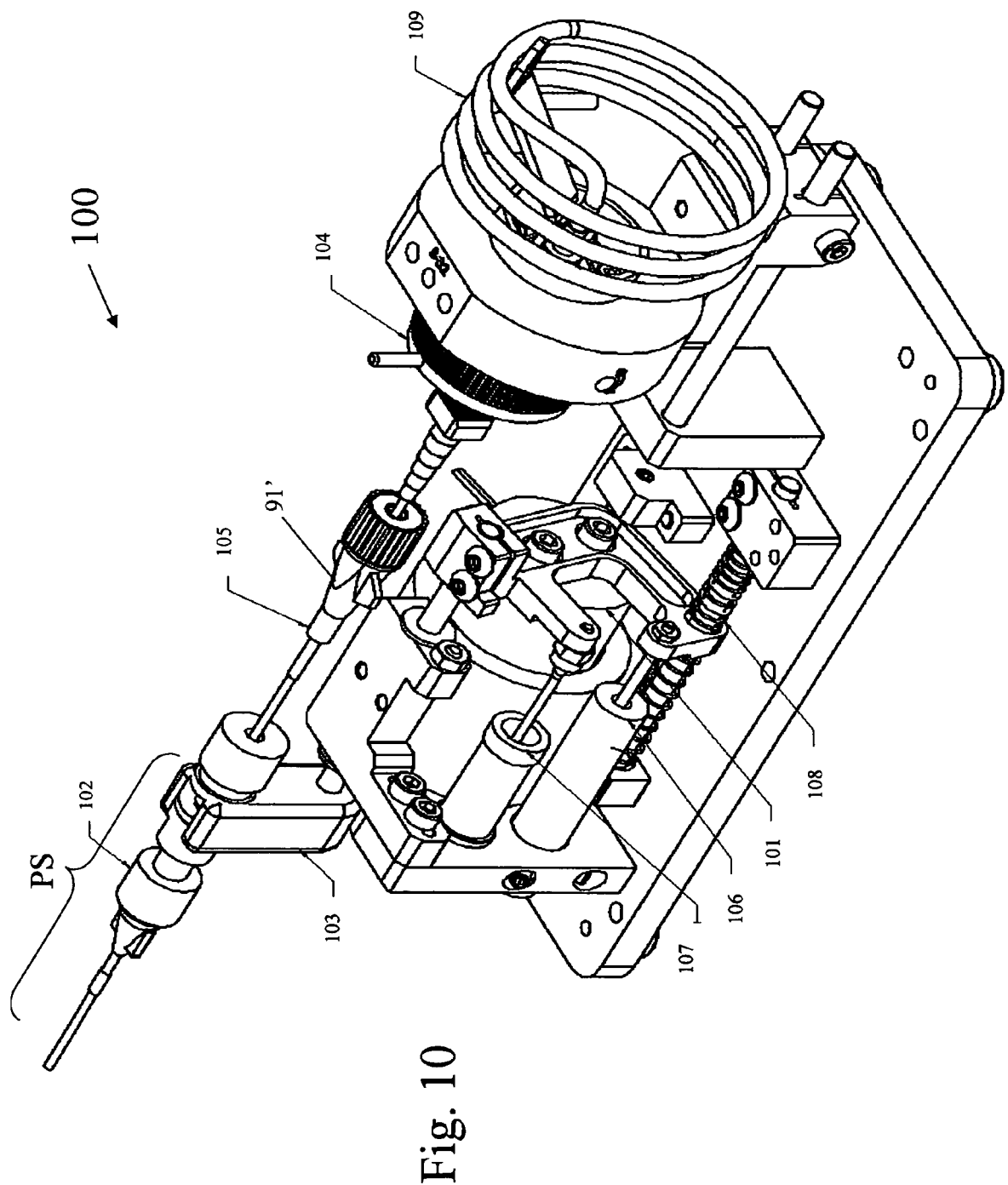
FIG. 10 is a schematic diagram that shows a portion of an imaging system incorporating a voice-coil actuator suitable for driving a push-pull mechanical linkage according to an illustrative embodiment of the invention.

Additionally, FIG. 10 shows another portion of a system 100 suitable for integrating with the push-pull imaging probes disclosed herein. The linkage includes an optical fiber inserted within a flexible metal (Nitinol or wound stainless-steel) tube that slides longitudinally inside a transparent plastic sheath filled with fluid. The proximal end of the sheath PS is driven by the moving core of a voice-coil actuator 101 (FIG. 10). Specifically, the voice-coil actuator 101 drives the imaging probe oscillating sheath 102 by actuating an oscillating probe mount 103. Typically, a probe connector and/or rotator 104 is in mechanical communication with the sheath 102. An imaging probe stationary core 105 that substantially encircles the sheath 102 and fiber is also shown. A Luer adaptor 91' is also shown in FIG. 10.

In some embodiments, the stationary core 105 may be manually rotated to change imaging position or the optical path at the catheter tip. A position feedback device 106 such a linear variable differential transformer can also be included in the system 100. A vibration damper 107 and centering springs 108 can also be incorporated. Finally, an optical fiber rotational strain relief loop 109 is shown. The loop 109 is adapted to couple to an imaging probe via a first port. In addition, the loop is adapted to couple to the sample arm of an interferometer via a second port. The loop is also adapted to slidably contain an optical fiber that extends through the sheath and into an imaging probe for insertion into a lumen of interest or positioning near a sample of interest.

Translation of the optical fiber relative to its sheath is achieved by pushing and pulling the sheath instead of the fiber which has distinct advantages described below. Since the middle section of the sheath itself is normally anchored to the main endoscope, needle probe, primary catheter, or even the bodily entrance point into which it is inserted, pushing the sheath proximal end away from the fiber proximal end has the effect of causing the distal end of the fiber to retract inside the distal sheath inside the lumen or structure being imaged. Hence the proximal portion of the fiber is stationary while the distal end translates relative to the imaged structure, providing scanning. To ensure uniform transmission of force, the fiber is glued to both the proximal and distal ends of the tube. The fluid provides lubrication and improves optical coupling between the distal tip of the optical fiber and the sheath. The voice-coil actuator provides constant-velocity translation under feedback control from a position sensor.

In one embodiment, the embodiments of FIGS. 9 and 10 are designed to translate the optical fiber smoothly over the entire scan length (typically a few millimeters to a centimeter) with a repetition rate high enough to avoid motion artifacts. The motion of the voice coil over each cycle is controlled by a bi-directional electronic signal applied to the voice coil, with position feedback provided by a linear-variable differential transformer, optical encoder, or similar type of sensor. To reduce the drive current required to reverse the direction coil at both ends of the travel, a pair of opposing springs is coupled to the shaft of the voice coil. An (optional) dashpot or equivalent device damps the mechanism to prevent vibrations. In applications that require less precise position control, a unidirectional (solenoid) electronic drive with spring return can be employed.

To orient the direction of the mirror at the distal end of the push-pull probe, a convenient means (element 104) is typically provided for rotating the optical fiber without interfering with its translation relative to its sheath. The configuration of the proximal end of the push-pull linkage shown in FIG. 9 and FIG. 10 accomplishes this objective. As shown, the fiber can rotate in any longitudinal position of the sheath, an advantage of moving the sheath not the fiber. Since the longitudinal position of the fiber remains stationary during the push-pull cycle, the fiber-optic connector 96 need only rotate under operator control, not oscillate back and forth. In FIG. 10, the fiber-optic connector (not shown) is disposed between elements 91' and 104. Not only does this design facilitate connection to the imaging system, but it also reduces the variability of the load presented to the linear actuator during the push-pull cycle. The optical fiber can be rotated either manually or automatically by a motor under servo control.

It should be appreciated that various aspects of the claimed invention are directed to subsets and substeps of the techniques disclosed herein. Further, the terms and expressions employed herein are used as terms of description and not of limitation, and there is no intention, in the use of such terms and expressions, of excluding any equivalents of the features shown and described or portions thereof, but it is recognized that various modifications are possible within the scope of the invention claimed. Accordingly, what is desired to be secured by Letters Patent is the invention as defined and differentiated in the following claims, including all equivalents.

What is claimed is:

1. An optical coherence tomography imaging probe for imaging a sample, the probe comprising:
   an elongate body having a wall defining a bore, a proximal end and distal end;
   the elongate body adapted to enclose a portion of a single slidable optical fiber within the bore, the single optical fiber having a longitudinal axis; and a first optical assembly attached to a distal end of the single optical fiber, wherein the first optical assembly comprises a beam director adapted to direct light emitted from the distal end of the single optical fiber and receive light reflected from the sample;
   a linear actuator disposed at the proximal end of the elongated body, the actuator adapted to affect relative linear motion between the elongate body and the single optical fiber; and
   a second optical assembly attached to the wall at the distal end of the elongate body, the second optical assembly comprising a reflector in optical communication with the first optical assembly, the reflector positioned at a predetermined angle to the longitudinal axis, the reflector adapted to direct the light through the distal end of the elongate body, receive light reflected from the sample and transmit it through the single optical fiber.

2. The optical coherence tomography imaging probe of claim 1 wherein the position of the reflector is adapted to cause the light to scan in a forward-viewing direction in response to the relative linear motion.

3. The optical coherence tomography imaging probe of claim 1 wherein the probe further comprises a stationary core that substantially encircles the elongate body, the stationary core adapted to change an imaging position at a catheter tip in response to rotation of the stationary core.

4. The optical coherence tomography imaging probe of claim 1 wherein the reflector and an optical window are constructed from a block of optical transparent material that attaches to the elongate body.

5. The optical coherence tomography imaging probe of claim 1 wherein the first optical assembly comprises an optical fiber with an angle-polished tip and the second optical assembly comprises the reflector with a pair of micro-lenses in a housing that attaches to the outside of the elongate body.

6. The optical coherence tomography imaging probe of claim 5 wherein the focal lengths and the positions of the micro-lenses are chosen to achieve a desired focal spot size and working distance.

7. The optical coherence tomography imaging probe 1 wherein the optical assembly comprises an optical fiber with an angle-polished tip and a reflector with a single gradient-index lens in a housing that attaches to the outside of the elongate body; the index profile and position of the gradient-index lens selected to achieve a desired focal spot size and working distance.

8. The optical coherence tomography imaging probe of claim 1 wherein the linear actuator comprises a voice coil.

9. The optical coherence tomography imaging probe of claim 1 wherein the linear actuator is adapted to cause the bore to move while the fiber remains stationary with respect to the actuator.

10. The optical coherence tomography imaging probe of claim 1 wherein the elongate body is fluid-filled and adapted to move back and forth around the optical fiber.

11. The optical coherence tomography imaging probe of claim 1 wherein the probe further comprises a metal tube that substantially ensheaths the optical fiber, except at its tip where light emerges, and an outer fluid-filled sheath that is adapted to move relative to the metal tube and optical fiber.

12. The optical coherence tomography imaging probe of claim 1, wherein the probe is configured for use in a sample arm of an optical coherence tomography system for applications related to scanning biological tissue.

13. The optical coherence tomography imaging probe of claim 12, wherein the either the sample arm of the optical coherence tomography system includes path length adjustment means, wherein such means automatically compensate optical path length changes induced by actuator scanning.

14. The optical coherence tomography imaging probe of claim 1 wherein a beam scans along a line in synchrony with the linear motion of the actuator.

15. The optical coherence tomography imaging probe of claim 1 wherein the elongate body further comprises a curved tip, at least a portion of the tip adapted to emit light in response to the linear motion.

16. An optical coherence tomography forward scanning system, the system comprising
   a linear actuator,
   a single mode optical fiber having an angled endface, the fiber mechanically coupled to the linear actuator, and
   a sheath having a distal end, a proximal end, and a wall defining a bore, the sheath comprising a reflector attached to the wall near the distal end at an angle such that motion of the optical fiber endface relative to the reflector directs light emitted from the side of the fiber from the endface to a plane substantially parallel to a circular cross-section of the fiber.

17. The system of claim 16 further comprising an optical fiber rotational strain relief apparatus, the apparatus in mechanical communication with the fiber.

* * * * *